United States Patent [19]

Fabian

[11] 4,393,700
[45] Jul. 19, 1983

[54] PROCESS AND TEST SPECIMEN FOR DETERMINING THE ADHESION TO GLASS OF INTERLAYERS FOR LAMINATED GLASS BY THE TENSILE SHEAR TEST

[75] Inventor: Klaus Fabian, Kriftel, Fed. Rep. of Germany

[73] Assignee: Hoechst Aktiengesellschaft, Frankfurt am Main, Fed. Rep. of Germany

[21] Appl. No.: 310,072

[22] Filed: Oct. 9, 1981

[30] Foreign Application Priority Data

Oct. 11, 1980 [DE] Fed. Rep. of Germany ....... 3038449

[51] Int. Cl.³ .............................................. G01N 3/24
[52] U.S. Cl. ..................................... 73/150 A; 73/842
[58] Field of Search ..................... 73/150 A, 827, 834, 73/842; 65/29

[56] References Cited

U.S. PATENT DOCUMENTS

3,850,033  11/1974  Schmitt ............................. 73/842 X

FOREIGN PATENT DOCUMENTS

276483  10/1970  U.S.S.R. ................................ 73/842

*Primary Examiner*—Jerry W. Myracle
*Attorney, Agent, or Firm*—Curtis, Morris & Safford

[57] ABSTRACT

Glass laminates used as safety glass consist of several sheets of glass united by adhesive interlayers. The bond strength of such interlayers may be determined in simple manner using a special test specimen by the tensile shear test. The test specimen is parallelipiped-like and the individual sheets thereof are divided each to form an obtuse fracture, the fractures facing the interlayer being staggered. The minimum force required for detaching the interlayer from the individual sheets of the glass laminate is taken as a measure for the bond strength.

4 Claims, 1 Drawing Figure

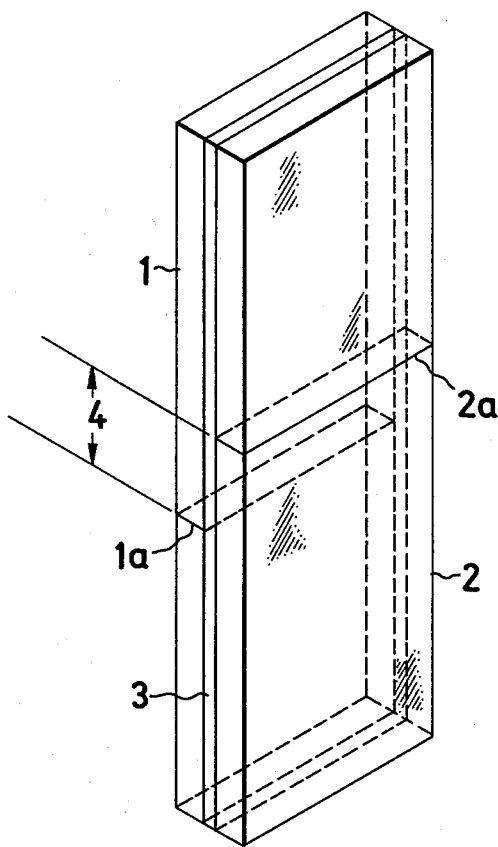

PROCESS AND TEST SPECIMEN FOR DETERMINING THE ADHESION TO GLASS OF INTERLAYERS FOR LAMINATED GLASS BY THE TENSILE SHEAR TEST

The present invention relates to a process for determining the adhesion to glass of interlayers for laminated glass by the tensile shear test and to a test specimen suitable for carrying out this process.

Glass laminates consist usually of several sheets of glass of identical or different thickness, that are united by an adhesive interlayer. This interlayer consists frequently of a thermoplastic material, in particular polyvinyl butyral (PVB), which is used, generally in the form of a sheet, for uniting the glass sheets. Glass laminates of the above type are used mainly as safety glass in the automotive and building industries. The interlayer shall prevent a detachment of fragments of glass from the laminate after impact thereon. The adhesion of the glass to the interlayer should not be excessively strong, otherwise the interlayer would be strained, disrupted and perforated at the point of the impact. An exact measurement of the bond strength of such interlayers is therefore important. This measurement requires an exact measuring method to be carried out in as simple a manner as possible and which permits the determination of objective reproducible data. It is the purpose of the present invention to provide such measuring method.

The present invention therefore relates to a process for determining the adhesion to glass of interlayers for laminated glass by the tensile shear test, which comprises subjecting to a tensile strain a substantially parallelepiped-like test specimen consisting of laminated glass, the individual sheets of which are divided to form an obtuse fracture, the edges of the fractures facing the interlayer being staggered, and determining the minimum force required to detach the interlayer from the individual sheets of the glass laminate.

The present invention relates furthermore to a test specimen useful for determining the adhesion to glass of interlayers for laminated glass by the tensile shear test, which test specimen consists of two rectangular sheets of glass 1 and 2 of from 30 to 100 mm length each, of from 5 to 25 mm width each and of from 3 to 10 mm thickness each, which are superposed congruently and united by an interlayer 3, each sheet being divided to form an obtuse fracture 1a and 2a, respectively, and the fractures being staggered in vertical direction to the longitudinal direction of the test specimen by the distance 4 and arranged in parallel manner.

The sheets of glass of the substantially parallelepiped-like test specimen have preferably a length of from 40 to 60 mm, a width of from 10 to 20 mm and a thickness of from 5 to 7 mm.

The plane limited by the edges of the fractures in contact with the interlayer and by the portions of the longitudinal sides of the sheets of glass therebetween is designated as shear plane. The size of the shear plane can be varied with a given width of the test specimen by changing the distance of the edges of the fractures from one another, this distance being 3 to 20 mm, preferably 4 to 10 mm. The surface area of the shear plane is normally from 0.5 to 2.5 cm$^2$. It is recommended to adjust the size of the shear plane to the expected shear strength. A shear plane of from 1.0 to 2.2 cm$^2$ surface area is indicated for a low shear strength, that is a shear strength of less than 2 MPa, a shear plane of from 0.7 to 1.0 cm$^2$ surface area for a medium shear strength, that is a shear strength of from 2 to 10 MPa, and a shear plane of from 0.5 to 0.8 cm$^2$ surface area for a very high shear strength, that is a shear strength of more than 10 MPa.

The process according to the invention is carried out preferably using the test specimens according to the invention. These may be made by cutting glass fragments from plane laminated glass or from simply or spherically curved laminated glass, for example from automobile windshields or sections thereof; in the latter cases the interlayer consists preferably of a polyvinyl butyral sheet having a thickness of from 0.1 to 1.5 mm preferably. Possible deviations of the data obtained on testing curved glass laminates may be substantially avoided by using test specimens of as little dimensions as possible.

The invention will be illustrated, by way of example, in the accompanying FIGURE representing a schematic view of the test specimen according to the invention.

Referring now to the FIGURE: The test specimen consists of two rectangular sheets of glass 1 and 2 united by an interlayer 3. The sheets of glass 1 and 2 have been divided to form an obtuse fracture 1a and 2a, respectively, and the fractures are staggered in vertical direction to the longitudinal direction of the test specimen by the distance 4 and arranged parallel to one another.

The test specimens are produced in the following manner:

Parallel cuts are effected on one face of a glass laminate using a usual glass cutter, the distance between the individual cuts corresponding to the desired length of the test specimens. Next, there are effected further cuts in parallel manner to the first cuts, these cuts limiting the shear plane, and finally parallel cuts are effected in vertical direction to the existing cuts, the distance of these vertical cuts corresponding to the desired width of the test specimens. Next, the sheet of glass is broken successively at the cuts defining the length of the test specimens, then at the cuts defining the width of the specimens and finally at the cuts limiting the shear plane. The second face of the glass laminate is cut and broken in the same manner, the cuts which limit the shear plane being staggered by a certain distance with respect to the corresponding cuts on the other face. As a result, there are obtained parallelepiped-like test specimens consisting of two rectangular sheets of glass superposed congruently and united by an interlayer, said sheets of glass being divided each in vertical direction to the longitudinal direction of the test specimen to form an obtuse fracture.

The process according to the invention is carried out preferably using a measuring apparatus appropriate for testing the tensile shear strength of various materials. This measuring apparatus is advantageously provided with recording means registering automatically the data obtained. As measuring apparatus there is used advantageously a tensile strength testing apparatus as specified in the German industrial standard DIN 51221, part 3.

The test specimen is fastened in the measuring apparatus by fixing means, preferably clamping jaws, which ensure a flawless transmission of the tensile strain from the measuring apparatus to the test specimen in the direction of the longitudinal axis of the test specimen. To this end, the fixing means are connected with the measuring apparatus preferably by means of ball cups and universal joints to compensate for possible rotational movement and oscillations during the measurement. The test specimen is fastened so as to extend in the center line of the fixing means. It must be fixed in slip-resistant manner. The test specimen is advantageously fastened such that the parts of the sheets of glass which cover the shear plane are not seized by the fixing means.

The process according to the invention is distinguished by the fact that it is carried out using test specimens producible in simple and rapid manner and using conventional measuring apparatuses that permit an objective judgement of the samples due to the data measured and calculated. The variation of the measured values obtained in a series of 20 measurements amounts to 5 to 10%.

The present invention is moreover illustrated in the following examples, where the tensile shear strength (MPa) is obtained by dividing the automatically measured breaking load (N) by the shear plane (mm$^2$).

EXAMPLE 1

20 Nearly parallelepiped-like test specimens of about 50 mm length and of about 15 mm width each are cut from a spherically curved asymmetric glass laminate. The cuts are effected such that the slightest curvature of the laminate extends in the longitudinal direction of the test specimens. The glass laminate consists of two sheets of glass of 3.0 mm and 2.0 mm thickness, respectively, which are united by a layer of 0.76 mm thickness made of a commercial polyvinyl butyral containing 20 weight % of vinyl alcohol units and 2 weight % of vinyl acetate units. Both sheets of glass of each test specimen are divided in the central part to form an obtuse fracture, the fractures being arranged parallel to one another and staggered by a certain distance, and in vertical direction to the longitudinal direction of each test specimen and the edges of the fractures facing the interlayer being arranged at a distance of about 7 mm from one another. The shear plane of each test specimen is measured. Next, each test specimen is subjected to a test for determining the tensile shear strength using a tensile testing apparatus according to the German industrial standard DIN 51 221, part 3. The tensile shear strength is calculated from the breaking load measured in each case. Further details can be seen from the following Table 1.

TABLE 1

| Test specimen No. | Shear plane Length (mm) | Width (mm) | Breaking load (N) | Tensile shear strength (MPa) |
|---|---|---|---|---|
| 1 | 14.5 | 6.7 | 198 | 2.04 |
| 2 | 14.6 | 6.9 | 215 | 2.13 |
| 3 | 15.0 | 7.0 | 234 | 2.23 |
| 4 | 15.1 | 6.9 | 226 | 2.17 |
| 5 | 14.6 | 7.0 | 204 | 2.00 |
| 6 | 13.8 | 7.1 | 241 | 2.46 |
| 7 | 14.2 | 6.9 | 232 | 2.37 |
| 8 | 15.3 | 7.0 | 247 | 2.31 |
| 9 | 14.0 | 7.0 | 233 | 2.28 |
| 10 | 14.7 | 7.0 | 236 | 2.29 |
| 11 | 14.5 | 7.0 | 218 | 2.15 |
| 12 | 13.5 | 6.8 | 208 | 2.23 |
| 13 | 14.4 | 6.6 | 235 | 2.47 |
| 14 | 14.9 | 6.7 | 228 | 2.28 |
| 15 | 13.7 | 6.8 | 217 | 2.33 |
| 16 | 15.5 | 6.6 | 218 | 2.13 |
| 17 | 14.2 | 6.7 | 217 | 2.28 |
| 18 | 14.3 | 6.4 | 193 | 2.11 |
| 19 | 14.8 | 6.5 | 217 | 2.26 |
| 20 | 14.1 | 6.4 | 190 | 2.11 |
| Average value: | | | | 2.23 |

EXAMPLE 2

Example 1 is repeated using a spherically curved asymmetric glass laminate, both sheets of which having a thickness of 3.0 mm each. The composition of the interlayer is unknown. The distance between the edges of the fractures is about 6 mm. Further details concerning this test for the tensile shear strength can be seen from the following Table 2.

TABLE 2

| Test specimen No. | Shear plane Length (mm) | Width (mm) | Breaking load (N) | Tensile shear strength (MPa) |
|---|---|---|---|---|
| 1 | 14.8 | 5.8 | 130 | 1.51 |
| 2 | 14.1 | 5.8 | 123 | 1.50 |
| 3 | 14.8 | 5.7 | 139 | 1.65 |
| 4 | 14.7 | 5.5 | 125 | 1.55 |
| 5 | 14.3 | 5.6 | 133 | 1.66 |
| 6 | 14.4 | 5.5 | 132 | 1.67 |
| 7 | 14.6 | 5.5 | 137 | 1.71 |
| 8 | 15.0 | 5.6 | 134 | 1.60 |
| 9 | 14.5 | 5.6 | 137 | 1.69 |
| 10 | 14.8 | 5.8 | 143 | 1.67 |
| 11 | 14.0 | 5.9 | 137 | 1.66 |
| 12 | 15.1 | 6.4 | 162 | 1.68 |
| 13 | 14.5 | 6.5 | 160 | 1.70 |
| 14 | 15.4 | 6.5 | 166 | 1.77 |
| 15 | 14.8 | 6.6 | 160 | 1.64 |
| 16 | 13.8 | 6.5 | 154 | 1.72 |
| 17 | 14.7 | 6.3 | 141 | 1.52 |
| 18 | 15.0 | 6.3 | 164 | 1.74 |
| 19 | 14.3 | 6.2 | 153 | 1.73 |
| 20 | 14.9 | 6.2 | 147 | 1.59 |
| Average value: | | | | 1.65 |

EXAMPLE 3

Example 1 is repeated using a plane symmetric laminate, the sheets of which have a thickness of 3.0 mm each. The composition of the interlayer is unknown. The distance between the edges of the fractures is about 5 mm. Further details concerning this test for the tensile shear strength can be seen from the following Table 3.

TABLE 3

| Test specimen No. | Shear plane Length (mm) | Width (mm) | Breaking load (N) | Tensile shear strength (MPa) |
|---|---|---|---|---|
| 1 | 14.6 | 5.0 | 376 | 5.15 |
| 2 | 15.1 | 5.2 | 393 | 5.00 |
| 3 | 14.4 | 5.0 | 360 | 5.00 |
| 4 | 15.0 | 5.1 | 370 | 4.84 |
| 5 | 14.8 | 5.2 | 380 | 4.93 |
| 6 | 14.9 | 5.1 | 374 | 4.92 |
| 7 | 14.9 | 4.9 | 457 | 4.89 |
| 8 | 14.5 | 5.0 | 335 | 4.62 |
| 9 | 14.8 | 5.0 | 365 | 4.93 |
| 10 | 14.9 | 5.1 | 375 | 4.93 |
| 11 | 14.3 | 5.0 | 360 | 5.04 |
| 12 | 14.8 | 4.9 | 371 | 5.12 |
| 13 | 14.9 | 5.1 | 400 | 5.26 |
| 14 | 14.6 | 4.9 | 356 | 4.98 |
| 15 | 14.8 | 5.1 | 361 | 4.78 |
| 16 | 14.3 | 4.7 | 326 | 4.85 |
| 17 | 14.7 | 4.9 | 341 | 4.73 |
| 18 | 14.3 | 5.1 | 340 | 4.66 |
| 19 | 15.0 | 4.8 | 367 | 5.10 |
| 20 | 15.2 | 4.8 | 354 | 4.85 |
| Average value: | | | | 4.93 |

EXAMPLE 4

Example 1 is repeated using a plane symmetric laminate, the sheets of which have a thickness of 3.0 mm each. The composition of the interlayer is unknown. The distance between the edges of the fractures is about 5 to 6 mm. Further details concerning this test for the tensile shear strength can be seen from the following Table 4.

TABLE 4

| Test specimen No. | Shear plane Length (mm) | Width (mm) | Breaking load (N) | Tensile shear strength (MPa) |
|---|---|---|---|---|
| 1 | 15.0 | 4.7 | 565 | 8.01 |
| 2 | 14.5 | 5.0 | 510 | 7.03 |
| 3 | 14.6 | 5.0 | 515 | 7.05 |
| 4 | 14.7 | 4.8 | 470 | 6.66 |
| 5 | 14.6 | 4.5 | 540 | 8.22 |
| 6 | 14.5 | 4.5 | 500 | 7.66 |
| 7 | 14.5 | 4.8 | 475 | 6.82 |
| 8 | 14.8 | 5.1 | 515 | 6.83 |
| 9 | 14.6 | 4.6 | 440 | 6.55 |
| 10 | 14.6 | 4.8 | 395 | 5.64 |
| 11 | 14.8 | 4.5 | 450 | 6.76 |
| 12 | 14.9 | 4.4 | 395 | 6.03 |
| 13 | 14.7 | 4.6 | 420 | 6.21 |
| 14 | 14.7 | 4.7 | 425 | 6.15 |
| 15 | 14.3 | 5.6 | 495 | 6.18 |
| 16 | 14.5 | 5.7 | 595 | 7.20 |
| 17 | 14.2 | 5.6 | 580 | 7.24 |
| 18 | 14.6 | 6.1 | 630 | 7.07 |
| 19 | 14.8 | 6.0 | 690 | 7.77 |
| 20 | 14.5 | 6.4 | 640 | 6.90 |
| Average value: | | | | 6.90 |

EXAMPLE 5

Example 1 is repeated using a plane symmetric laminate, the sheets of which have a thickness of 3.0 mm each. The composition of the interlayer is unknown. The distance between the edges of the fractures is about 6 mm. Further details concerning this test for the tensile shear strength can be seen from the following Table 5.

TABLE 5

| Test specimen No. | Shear plane Length (mm) | Width (mm) | Breaking load (N) | Tensile shear strength (MPa) |
|---|---|---|---|---|
| 1 | 16.1 | 6.0 | 1,050 | 10.87 |
| 2 | 14.8 | 5.7 | 1,050 | 11.82 |
| 3 | 15.0 | 6.7 | 1,000 | 11.11 |
| 4 | 14.9 | 5.9 | 995 | 11.32 |
| 5 | 14.7 | 6.0 | 1,085 | 12.30 |
| 6 | 14.8 | 5.9 | 1,105 | 12.65 |
| 7 | 15.0 | 5.8 | 1,095 | 12.69 |
| 8 | 14.8 | 5.8 | 875 | 10.19 |
| 9 | 15.1 | 5.9 | 1,080 | 12.12 |
| 10 | 14.5 | 5.9 | 985 | 11.51 |
| 11 | 14.7 | 6.0 | 1,030 | 11.68 |
| 12 | 14.4 | 6.0 | 1,020 | 11.81 |
| 13 | 14.5 | 5.9 | 990 | 11.57 |
| 14 | 14.6 | 5.8 | 865 | 10.21 |
| 15 | 15.2 | 5.8 | 1,085 | 12.31 |
| 16 | 14.8 | 5.9 | 1,115 | 12.77 |
| Average value: | | | | 11.7 |

What is claimed is:

1. A process for determining the adhesion to glass of interlayers for laminated glass by the tensile shear test, which comprises subjecting to a tensile strain a substantially parallelepiped-like test specimen consisting of laminated glass, the individual sheets of glass of which are divided to form an obtuse fracture, the edges of the fractures facing the interlayer being staggered, and determining the minimum force required to detach the interlayer from the individual sheets of the glass laminate.

2. The process of claim 1, which comprises effecting the tensile strain transversely to the fractures, which latter are arranged parallel to one another and vertically to the longitudinal axis of the test specimen.

3. The process of claim 1, which comprises employing a test specimen consisting of two rectangular sheets of glass of from 30 to 100 mm length each, of from 5 to 25 mm width each and of from 3 to 10 mm thickness each, which are superposed congruently and united by an interlayer, each sheets being divided to form an obtuse fracture and the fractures being arranged vertically to the longitudinal direction of the test specimen and parallel to one another, and a measuring apparatus appropriate for determining the tensile shear strength.

4. A test specimen for determining the adhesion to glass of interlayers for laminated glass by the tensile shear test, consisting of two rectangular sheets of glass of from 50 to 100 mm length each, of from 5 to 25 mm width each and of from 3 to 10 mm thickness each, said sheets being divided to form an obtuse fracture each and said fractures being arranged vertically to the longitudinal direction of the test specimen and parallel to one another and staggered by a certain distance.

* * * * *